United States Patent [19]
Bellasio

[11] 3,935,236
[45] Jan. 27, 1976

[54] AMINOPROPANOL SUBSTITUTED ISOCHROMANONES AND PHTHALIDES

[75] Inventor: Elvio Bellasio, Como, Italy

[73] Assignee: Gruppo Lepetit, S.p.A., Milan, Italy

[22] Filed: May 24, 1974

[21] Appl. No.: 473,099

[30] Foreign Application Priority Data
May 30, 1973 United Kingdom............... 25678/73

[52] U.S. Cl......... 260/343.2 R; 260/343.3; 424/279
[51] Int. Cl.².............. C07D 307/88; C07D 311/76
[58] Field of Search................... 260/343.2 R, 343.3

[56] References Cited
UNITED STATES PATENTS
3,663,570  5/1972  Sato et al......................... 260/343.2

Primary Examiner—James A. Patten
Attorney, Agent, or Firm—Theodore Post; C. Kenneth Bjork

[57] ABSTRACT

Aminopropanols with β-blocking activity having the general formula

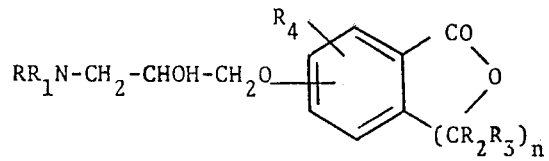

wherein R is hydrogen, $C_1$-$C_4$ alkyl or hydroxy-($C_2$-$C_4$) alkyl, $R_1$ is $C_1$-$C_4$ alkyl or hydroxy-($C_2$-$C_4$) alkyl; $R_2$ and $R_3$ each independently represent hydrogen or $C_1$-$C_2$ alkyl, $R_4$ is hydrogen or alkoxy of 1 to 4 C, $n$ is the number 1 or 2; and their pharmaceutically acceptable acid addition salts.

5 Claims, No Drawings

AMINOPROPANOL SUBSTITUTED ISOCHROMANONES AND PHTHALIDES

BACKGROUND OF THE INVENTION

A series of compounds displaying β-blocking activity is reported in a review by A. M. Karow et al., published in "Progress in Drug Research", Vol. 15, page 103 (Birkhauser Verlag Basel, 1971).

The substances which have this biological effect generally must have an alkylaminopropanol chain attached to an aromating ring system, sometime by an ethereal link.

SUMMARY OF THE INVENTION

This invention is concerned with new pharmacologically active compounds. More particularly, the new compounds with which the invention is concerned are aminopropanol derivatives of the general formula

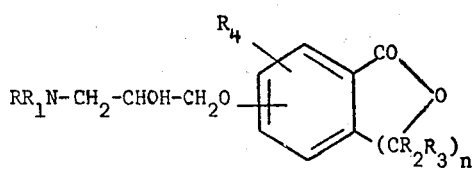

wherein R is hydrogen, $C_1$-$C_4$ alkyl or hydroxy-($C_2$-$C_4$) alkyl, $R_1$ is $C_1$-$C_4$ alkyl or hydroxy-($C_2$-$C_4$) alkyl; $R_2$ and $R_3$ each independently represent hydrogen or $C_1$-$C_2$ alkyl, $R_4$ is hydrogen or alkoxy of 1 to 4 C, $n$ is the number 1 or 2; and the pharmaceutically acceptable acid addition salts thereof. In the specification and in the claims, it is understood that the substituents on the aromatic ring may be in all possible mutual positions. Moreover, the invention is further characterized in that, when $n$ is the number 2, the symbol $R_2$ and $R_3$ may have a different meaning in each of the two groups $CR_2R_3$: for instance in the group $CR_2R_3$ which is bound to the aromatic ring, both $R_2$ and $R_3$ may represent hydrogen and in the group $CR_2R_3$ which is bound to the oxygen atom both $R_2$ and $R_3$ may represent $C_1$-$C_2$ alkyl or one of them represents hydrogen and the other represents $C_1$-$C_2$ alkyl.

In the specification and claims the term $C_1$-$C_4$ alkyl refers to aliphatic radicals containing 1 to 4 carbon atoms such as methyl, ethyl, propyl, isopropyl, butyl, isobutyl and tert-butyl.

The term "$C_1$-$C_2$ alkyl" identifies the groups methyl and ethyl. In the "hydroxy-($C_2$-$C_4$)alkyl" groups the $C_2$-$C_4$ alkyl portion may be straight or branched; said groups may identify for istance, 2-hydroxyethyl, 2-hydroxypropyl, 3-hydroxypropyl, 2-hydroxybutyl, 2-hydroxy-2-methylpropyl radicals.

In the term "lower alkoxy" the alkyl portion is defined in the same way as the term $C_1$-$C_4$ alkyl. Representative lower alkoxy groups are for instance methoxy, ethoxy, propoxy and butoxy.

A preferred group of compounds comprises those compounds of formula I where if $n$ is 1, R is hydrogen, $R_1$ is propyl, isopropyl, butyl, isobutyl or tert-butyl, $R_2$ and $R_3$ represent hydrogen, $R_4$ represent hydrogen or methoxy; if $n$ is 2, the symbols R, $R_1$ and $R_4$ have the same meanings as in the previous case, $R_2$ and $R_3$ in the groups $CR_2R_3$ which is bound to the aromatic ring both represent hydrogen while in the group which is bound to the oxygen atom each of them may independently represent hydrogen, methyl or ethyl.

The acids which may form pharmaceutically acceptable salts are for instance hydrochloric acid, hydrobromic acid, sulfuric acid, acetic acid, oxalic acid, p-toluenesulfonic acid, methanesulfonic acid, maleic acid, succinic acid, citric acid and the like.

The new compounds of the invention show a high activity on β-receptors. More particularly, they are long acting β-adrenergic blocking agents and are therefore useful in the treatment of cardio-circulatory diseases such as angina pectoris, cardiac arrhytmies and hypertension. Their activity is associated with a low toxicity.

The compounds of this invention are prepared by reacting a hydroxy derivative of the formula II with a 1-halo-2,3-epoxypropane preferably in the presence of a catalytic amount of an organic base to obtain the epoxy derivative III which in turn is contacted with a selected amine IV according to the following scheme where R, $R_1$, $R_2$, $R_3$, $R_4$ and $n$ have the same meaning as before

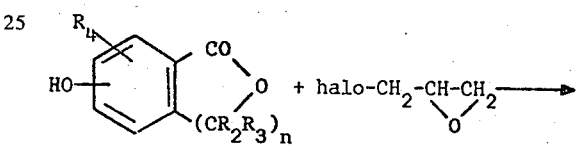

II

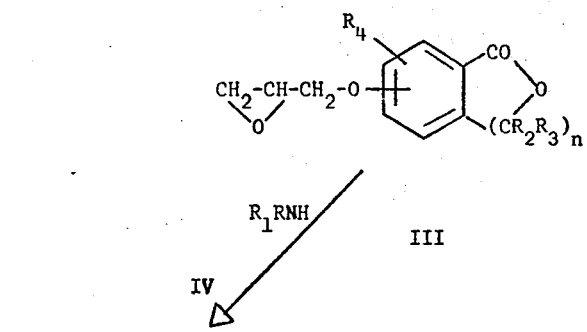

III

IV

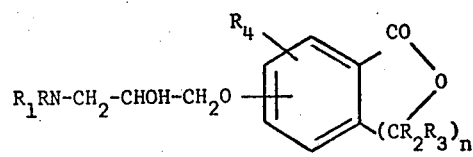

I

The compound I is usually isolated as an acid addition salt such as hydrochloride, hydrobromide and oxalate. The starting hydroxy compounds II are literature compounds or are prepared according to common procedures as described in the examples.

In the actual practice the first reaction step between the hydroxycompound and the haloepoxypropane is carried out by heating for 3–8 hours at about 100°C a mixture of the two reactants preferably in the presence of a few drops of an organic base such as piperidine. Said mixture generally contains a large excess of the haloepoxypropane which in this way, acts also as a solvent. When the reaction is complete the unreacted compound is eliminated by distilling under vacuum. The ring opening of the epoxide III is effected by dissolving the compound in an organic solvent such as, for instance, a lower alkanol and by successively adding an excess of the predeterminated amine $R_1RNH$. The reaction mixture is maintained for several hours at a temperature from about 0 to about the boiling temperature until thin layer chromatography of the solution shows that the reaction is complete.

Evaporation of the solvents affords a crude residue that is dissolved in a lower alkanol and then transformed into the corresponding salt through saturation of the solution with dry hydrogen halide or by addition of a suitable acid containing solution.

As mentioned before the compounds which the present invention is concerned with display marked $\beta$-adrenergic blocking activity. Some representative experiments in anesthesized rats showed $ED_{50}$ values, i.e. the amount of compound required to reach a 50 percent effect in antagonizing isopropylnoradrenaline induced tachycardia and pressor response, ranging from about 0.003 to about 0.3 mg/kg i.v.

The following table reports the value of $ED_{50}$ of some compounds in antagonizing isopropylnoradrenaline induced tachycardia in conscious dogs. As a standard compound pronethalol was taken into consideration. Pronethalol, i.e. 2-isopropylamino-1-(1-naphthyl)-ethanol, is a known $\beta$-blocking agent.

TABLE

| Compound of Example | $ED_{50}$ mg/Kg i.v. | $LD_{50}$ mg/Kg os |
|---|---|---|
| 1 | 0.01 | >500 |
| 2 | 0.3 | >500 |
| 5 | 0.003 | >500 |
| 6 | 0.1 | >500 |
| 7 | 0.055 | >500 |
| 8 | 0.07 | >500 |
| 9 | 0.1 | >500 |
| 10 | 0.1 | >500 |
| 12 | 0.003 | >500 |
| 13 | 0.005 | >500 |
| 14 | 0.1 | >500 |
| 15 | 0.018 | >500 |
| Pronethalol | 0.55 | 330 |

In the conscious dogs the compounds proved to be active also by oral administration. The invention compounds can be advantageously administered orally or by intravenous and subcutaneous route. For this purpose, they are compounded into suitable pharmaceutical forms, such as, for instance, tablets, capsules, suspensions and solutions. The dosage unit may contain the usual excipients like starch, gums, fatty acids, sugars, preservatives, solvents and other pharmaceutical carriers. The dosage range is from 0.001 to about 3 mg/kg. of body weight per day, preferably administered in divided doses.

Accordingly the present invention provides a therapeutic composition comprising as the active ingredient a compound of the invention together with a pharmaceutically acceptable carrier.

DESCRIPTION OF SOME PREFERRED EMBODIMENTS

The present invention is illustrated but not limited by the following examples.

EXAMPLE 1

7-(2-Hydroxy-3-isopropylamino-propoxy)-phthalide hydrochloride.

A mixture of 18 g. (0.12 mole) of 7-hydroxyphthalide, 180 g. of 1-chloro-2,3-epoxypropane (2 moles) and 0.5 ml. of piperidine is heated at 100°C for about 5 hours and then the unreacted 1-chloro-2,3-epoxypropane is distilled off in vacuo. The residue is crystallized successively from methanol and ethyl acetate. Yield 12 g. (48%). M.p. 88°–90°C.

One gram of the so obtained 7-(2,3-epoxy-propoxy)-phthalide (0.00485 mole) is dissolved in 150 ml. of methanol and 3.5 g. of isopropylamine (0.06 mole) are added to the solution at about 20°C. The solution is allowed to stand overnight and, after thin layer chromatography has shown that the starting epoxide has been completely consumed, the mixture is evaporated in vacuo and the residue is dissolved in methanol. Saturation of the obtained organic solution with dry hydrogen chloride gives a precipitate which is 7-(2-hydroxy-3-isopropylamino-propoxy)-phthalide hydrochloride. Yield 0.87 g. (60%); m.p. 195°–6°C.

EXAMPLE 2

6-(2-Hydroxy-3-isopropylamino-propoxy)-phthalide.

The title compound is prepared according to the procedure of Example 1 by utilizing 6-hydroxyphthalide in the place of 7-hydroxyphthalide. The compound is isolated as a free base; m.p. 95°–7°C. The intermediate 6-(2,3-epoxy-propoxy)-phthalide melts at 120°–1°C.

EXAMPLE 3

5-(2-Hydroxy-3-isopropylamino-propoxy)-phthalide hydrochloride.

The title compound is prepared according to the procedure of Example 1 by utilizing 5-hydroxyphthalide in the place of 7-hydroxyphthalide; m.p. 202°–3°C. The intermediate 5-(2,3-epoxypropoxy)-phthalide melts at 145°–7°C.

EXAMPLE 4

4-(2-Hydroxy-3-isopropylamino-propoxy)-phthalide hydrochloride.

The title compound is prepared according to the procedure of Example 1 by utilizing 4-hydroxyphthalide in the place of 7-hydroxyphthalide; m.p. 198°–200°C. The intermediate 4-(2,3-epoxypropoxy)-phthalide melts at 142°–4°C.

EXAMPLE 5

7-(2-Hydroxy-3-tert-butylamino-propoxy)-phthalide hydrochloride.

The title compound is obtained according to the procedure of Example 1 by employing ter-butylamine instead of isopropylamine; m.p. 156°–7°C.

EXAMPLE 6

7-(2-Hydroxy-3-isopropylamino-propoxy)-1-isochromanone hydrochloride.

The title compound is obtained according to the procedure of Example 1 by utilizing 7-hydroxy-1-isochromanone in the place of 7-hydroxy-phthalide; m.p. 183°–5°C. The intermediate 7-(2,3-epoxy-propoxy)-1-isochromanone melts at 94°–6°C.

EXAMPLE 7

7-(2-Hydroxy-3-tert-butylamino-propoxy)-1-isochromanone hydrochloride.

The title compound is obtained according to the procedure of Example 1 by utilizing 7-hydroxy-1-isochromanone in the place of 7-hydroxyphthalide and tert-butylamine in the place of isopropylamine; m.p. 199°–201°C.

EXAMPLE 8

4-(2-Hydroxy-3-tert-butylaminopropoxy)-phthalide hydrochloride

The title compound is obtained according to the procedure of Example 1 by employing 4-hydroxyphthalide in the place of 7-hydroxyphthalide and tert-butylamine in the place of isopropylamine; m.p. 251°–2°C.

EXAMPLE 9

6-(2-Hydroxy-3-tert-butylamino-propoxy)-phthalide hydrochloride

The title compound is obtained according to the procedure of Example 1 by employing 6-hydroxyphthalide in the place of 7-hydroxyphthalide and tert-butylamine in the place of isopropylamine; m.p. 203°–5°C.

EXAMPLE 10

7-(2-Hydroxy-3-isobutylamino-propoxy)-phthalide hydrochloride

The title compound is obtained according to the procedure of Example 1 by employing tert-butylamine in the place of isobutylamine; m.p. 149°–51°C.

EXAMPLE 11

5-(2-Hydroxy-3-tert-butylamino-propoxy)-phthalide hydrochloride

The title compound is obtained according to the procedure of Example 1 by employing 5-hydroxyphthalide in the place of 7-hydroxyphthalide and tert-butylamine in the place of isopropylamine; m.p. 182°–4°C.

EXAMPLE 12

8-(2-Hydroxy-3-tert-butylamino-propoxy)-1-isochromanone hydrochloride

The title compound is obtained according to the procedure of Example 1 by employing 8-hydroxy-1-isochromanone in the place of 7-hydroxyphthalide and tert-butylamine in the place of isopropylamine; m.p. 144°–5°C.

EXAMPLE 13

5-(2-Hydroxy-3-tert-butylamino-propoxy)-7-methoxy-3-methyl-1-isochromanone hydrochloride The title compound is obtained according to the procedure of Example 1 by employing 5-hydroxy-3-methyl-7-methoxy-1-isochromanone in the place of 7-hydroxyphthalide and tert-butylamine in the place of isopropylamine; m.p. 232°–33°C.

EXAMPLE 14

3-Ethyl-5-(2-hydroxy-3-tert-butylamino-propoxy)-7-methoxy-1-isochromanone hydrochloride The title compound is obtained according to the procedure of Example 1 by employing 3-ethyl-5-hydroxy-7-methoxy-1-isochromanone in the place of 7-hydroxyphthalide and tert-butylamine in the place of isopropylamine; m.p. 124°–5°C.

EXAMPLE 15

5-(2-Hydroxy-tert-butylamino-propoxy)-7-methoxy-3,3-dimethyl-1-isochromanone oxalate.

The title compound is obtained according to the procedure of Example 1 by employing 5-hydroxy-7-methoxy-3,3-dimethyl-1-isochromanone in the place of 7-hydroxyphthalide, tert-butylamine in the place of isopropylamine and oxalic acid instead of hydrogen chloride; m.p. 191°–3°C.

EXAMPLES 16–22

According to the procedure described in the previous examples the following compound may be prepared:
16) - 8-(2-Hydroxy-3-isopropylamino-propoxy)-1-isochromanone oxalate. M.p. 147°–9°C.
17) - 7-(2-Hydroxy-3-isopropylamino-propoxy)-5-methoxyphthalide hydrochloride
18) - 7-(2-Hydroxy-3-tert-butylamino-propoxy)-5-methoxyphthalide hydrochloride
19) - 7-(2-Hydroxy-3-isopropylamino-propoxy)-3-methylphthalide hydrochloride
20) - 7-(2-Hydroxy-3-tert-butylamino-propoxy)-3-methylphthalide hydrochloride
21) - 7-(2-Hydroxy-3-tert-butylamino-propoxy)-6-methoxyphthalide hydrochloride
22) - 7-(2-Hydroxy-3-isopropylamino-propoxy)-6-methoxyphthalide hydrochloride

Preparations of intermediates

The hydroxyphthalides used as the starting materials are prepared as described in the literature. The hydroxyisochromanones are prepared according to the procedures described below:

7-Hydroxy-1-isochromanone.

The title compound is obtained by reduction of 7-nitro-1-isochromanone to amino followed by reaction with sodium nitrite in acidic medium and decomposition of the obtained diazonium salt. All processes are carried out according to common procedures which are used for analogous compounds. The reduction is carried out by means of iron powder in the presence of hydrochloric acid while the conversion of the amino group to diazonium salt is effected by introducing sodium nitrite into a solution of the amino compound in dilute sulfuric acid. The diazonium salt is decomposed by dropping the solution into boiling 50% sulfuric acid. 7-Hydroxy-1-isochromanone may be crystallized from water. M.p. 181°–2°C.

The starting 7-nitro-1-isochromanone (M.p. 124°–5°C) is prepared from 1-isochromanone according to the same procedure described by J. Tirouflet for the nitration of phthalide. (Bull. Soc. Sci. Bretagne, No. 26, 7, 1951; Chemical Abstract, 47, 8692, 1953).

8-Hydroxy-1-isochromanone

This compound is obtained by demethylation of the corresponding 8-methoxy derivative (N.S. Narasimhan et al., Chem. Comm. 1970, 1552).

The demethylation is carried out by heating for 4 hours at 175°C with an excess of pyridine hydrochloride according to a known procedure for cleavage of ethers. M.p. 58°–60°C (from light petroleum).

5-Hydroxy-7-methoxy-3-methyl-1-isochromanone

3-Hydroxy-5-methoxybenzoic acid methyl ester is reacted with allyl bromide in the presence of potassium carbonate to give 3-allyloxy-5-methoxybenzoic acid methyl ester. B.p. 128°–30°C/0.4 mmHg. The ester is hydrolized to the corresponding acid with 20% potassium hydroxide in aqueous ethanol. The acid (m.p. 85°–7°C) when heated for 2 hours at 230°C undergoes Claisen rearrangement and cyclization to the title compound which melts at 195°–7°C.

3-Ethyl-5-hydroxy-7-methoxy-1-isochromanone

The compound is obtained according to the procedure described above by using 3-chloro-1-butene instead of allyl bromide. M.p. 167°–8°C.

5-Hydroxy-7-methoxy-3,3-dimethyl-1-isochromanone

The compound is obtained according to the procedure described before by using 3-chloro-2-methyl-1-propane instead of allyl bromide. M.P. 231°–33°C.

I claim:

1. A compound of the formula I

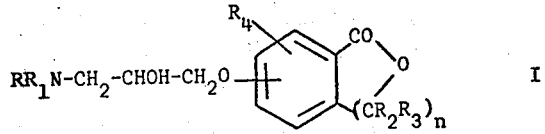

wherein R is hydrogen, $C_1$-$C_4$ alkyl or hydroxy-($C_2$-$C_4$) alkyl; $R_1$ is $C_1$-$C_4$ alkyl or hydroxy-($C_2$-$C_4$) alkyl; $R_2$ and $R_3$ each independently represent hydrogen or $C_1$-$C_2$ alkyl, $R_4$ is hydrogen or alkoxy of 1 to 4 C, n is the number 1 or 2; and the pharmaceutically acceptable acid addition salts thereof.

2. A compound as in claim 1 which is 7-(2-hydroxy-3-tert-butylamino-propoxy)-phthalide hydrochloride.

3. A compound as in claim 1 which is 8-(2-hydroxy-3-tert-butylamino-propoxy)-1-isochromanone hydrochloride.

4. A compound as in claim 1 which is 5-(2-hydroxy-3-tert-butylamino-propoxy)-7-methoxy-3-methyl-1-isochromanone hydrochloride.

5. A compound as in claim 1 which is 7-(2-hydroxy-3-isopropylamino-propoxy)-phthalide hydrochloride.

* * * * *

UNITED STATES PATENT AND TRADEMARK OFFICE
CERTIFICATE OF CORRECTION

PATENT NO. : 3,935,236
DATED : January 27, 1976
INVENTOR(S) : Elvio Bellasio

It is certified that error appears in the above-identified patent and that said Letters Patent are hereby corrected as shown below:

Column 8, line 5, "propane" should read --propene--.

Signed and Sealed this twenty-ninth Day of June 1976

[SEAL]

Attest:

RUTH C. MASON
*Attesting Officer*

C. MARSHALL DANN
*Commissioner of Patents and Trademarks*